United States Patent [19]
Ackland et al.

[11] Patent Number: 5,196,341
[45] Date of Patent: Mar. 23, 1993

[54] APPARATUS FOR DETECTING MICRO-ORGANISMS

[75] Inventors: Martin R. Ackland; Roderick M. De'Ath, both of Wantage, England

[73] Assignee: CMB Foodcan plc, United Kingdom

[21] Appl. No.: 759,601

[22] Filed: Sep. 1, 1989

Related U.S. Application Data

[63] Continuation of Ser. No. 15,927, Feb. 18, 1987, abandoned.

[30] Foreign Application Priority Data

Mar. 19, 1986 [GB] United Kingdom ............... 8606807

[51] Int. Cl.$^5$ .................. C12Q 1/04; C12N 13/00; C12M 1/34; G01M 3/04
[52] U.S. Cl. ........................... 435/291; 435/34; 435/173; 435/287; 422/102; 340/605; 73/49.2
[58] Field of Search .............. 435/173, 287, 291, 296, 435/34; 422/82.01, 82.02, 102, 104, 119; 73/40.5 R, 49.2 R, 49.2 T; 340/605

[56] References Cited

U.S. PATENT DOCUMENTS

| 3,403,081 | 9/1968 | Rohrback et al. | 435/291 |
|---|---|---|---|
| 3,743,581 | 7/1973 | Cady et al. | 435/291 |
| 3,789,297 | 1/1974 | Frolich | 340/605 |
| 3,889,247 | 6/1975 | Voll | 340/605 |
| 4,288,544 | 9/1981 | Suzuki et al. | 435/39 |
| 4,568,925 | 2/1986 | Butts | 340/605 |
| 4,653,337 | 3/1987 | Ackland et al. | 73/866.5 |
| 4,801,546 | 1/1989 | Ackland | 435/291 |

FOREIGN PATENT DOCUMENTS

WO85/00225 1/1985 PCT Int'l Appl. .
2142433 1/1985 United Kingdom .
2171982 9/1986 United Kingdom .

OTHER PUBLICATIONS

Frobisher et al., *Microbiology in Health and Disease* p. 194, 1978.

*Primary Examiner*—Robert J. Warden
*Assistant Examiner*—T. A. Trembley
*Attorney, Agent, or Firm*—Diller, Ramik & Wight

[57] ABSTRACT

Apparatus for detecting micro-organisms comprises a sample container releasably received in a container-mounting member which comprises a spillage containment vessel. The sample container has secured to its base a socket member which nests with the inner surface of the spillage containment vessel. Spillage detection means comprises a pair of electrical probes in the base of the vessel.

10 Claims, 2 Drawing Sheets

APPARATUS FOR DETECTING MICRO-ORGANISMS

This application is a continuation of application Ser. No. 07/015,927 filed Feb. 18, 1987, now abandoned.

BACKGROUND OF THE INVENTION

1. Field of the Invention

The present invention relates to apparatus for use in detecting micro-organisms in samples of substances such as foods, beverages pharmaceuticals or pathological samples, such as blood.

2. Description of the Prior Art

Electrochemical methods for detecting the growth of micro-organisms in such samples have been proposed and include measuring conductance, impedance or potential difference changes in the samples. Apparatus suitable for carrying out one such method has been described and claimed in our co-pending U.K. Patent Application No. 8602980. That apparatus comprises a plurality of containers for holding the microbiological samples to be tested and a container-mounting rack into which the containers are inserted for tests to be carried out on the samples.

The apparatus suffers a disadvantage that the sample containers are not particularly stable, either when they are free-standing out of the rack or when received by the rack. This is because of the relatively tall, yet narrow socket member secured to the container which acts both as a base on which to stand the container upright when it is not loaded into the rack and as a means of releasable connection between the container and the rack when the container is received thereby.

A further disadvantage of this known apparatus is that, whilst the apparatus provides means for catching any inadvertent spillage of sample material into the rack by providing a spillage-containment vessel at each station where a sample container is to be located in the rack, there are no means for detecting whether any such spillage into a vessel has occurred. Thus, it would be possible for a container subsequently loaded at that particular station to become contaminated.

SUMMARY OF THE INVENTION

It is an object of the present invention to provide apparatus for detecting micro-organisms in a sample, in which the sample containers are stable both in and out of the container-mounting member, or rack.

It is a further object of the present invention to provide apparatus for detecting micro-organisms in a sample, in which spillage into a containment vessel can be detected.

In accordance with the present invention there is provided apparatus for detecting micro-organisms in a sample, comprising a container for holding the sample having at least one electrode contactable with the sample therein, a socket member secured to the container, and a container-mounting member having means for receiving and locating the container, wherein said receiving and locating means are provided, at least in part, by a spillage-containment vessel adapted to contain spillage of sample material into the container-mounting member.

Preferably, the spillage-containment vessel and socket member are of complementary cross-section and, when the container is received by the container-mounting member, the socket member is in nesting relation to said vessel.

Suitably, the outer surface of the socket member nests with the inner surface of the spillage containment vessel, said outer surface being substantially right cylindrical and having an axial extent less than its diameter.

Since the socket member acts as the base for the container when it is free-standing i.e. when not received by the container-mounting member, such a shape of socket member ensures considerable stability when the container is stood upright.

The container-mounting member suitably comprises electrical contact means for electrical connection with the or each respective said electrode of the container and the apparatus may further comprise orientation means between the socket member and the spillage-containment vessel, whereby, when the container is received by the container-mounting member, the or each electrode is at a predetermined orientation to the container-mounting member and hence to the or each respective electrical contact means.

The orientation means may suitably comprise a key and keyway, one of which is provided on the socket member and the other on the spillage containment vessel.

Preferably, the spillage containment vessel comprises stop means cooperable with the container or the socket member, which stop means are adapted to limit travel of the container relative to the container-mounting member when being received thereby.

In accordance with a preferred embodiment of the present invention, the spillage containment vessel has in its base electrical probe means contactable with spillage of sample material in the vessel, which probe means are adapted to detect presence of spillage of sample material in the vessel.

Preferably, said electrical probe means comprises two electrical probes located in the base of the vessel, the apparatus further comprising means for applying an electrical potential across said two probes, whereby a change of resistance between the probes indicates presence of spillage in the vessel.

The container may further comprise an elastomeric bung through which sample material may be injected into the container and tamper-proof cap means protecting the bung until the container is required for use.

The apparatus may further comprise a removable collar, co-operable with said tamper-proof cap means by slipping friction, and provided with interengagement means co-operable with the container-mounting member for releasable retention of the container by the container-mounting member.

DETAILED DESCRIPTION OF THE INVENTION

Figure 1:
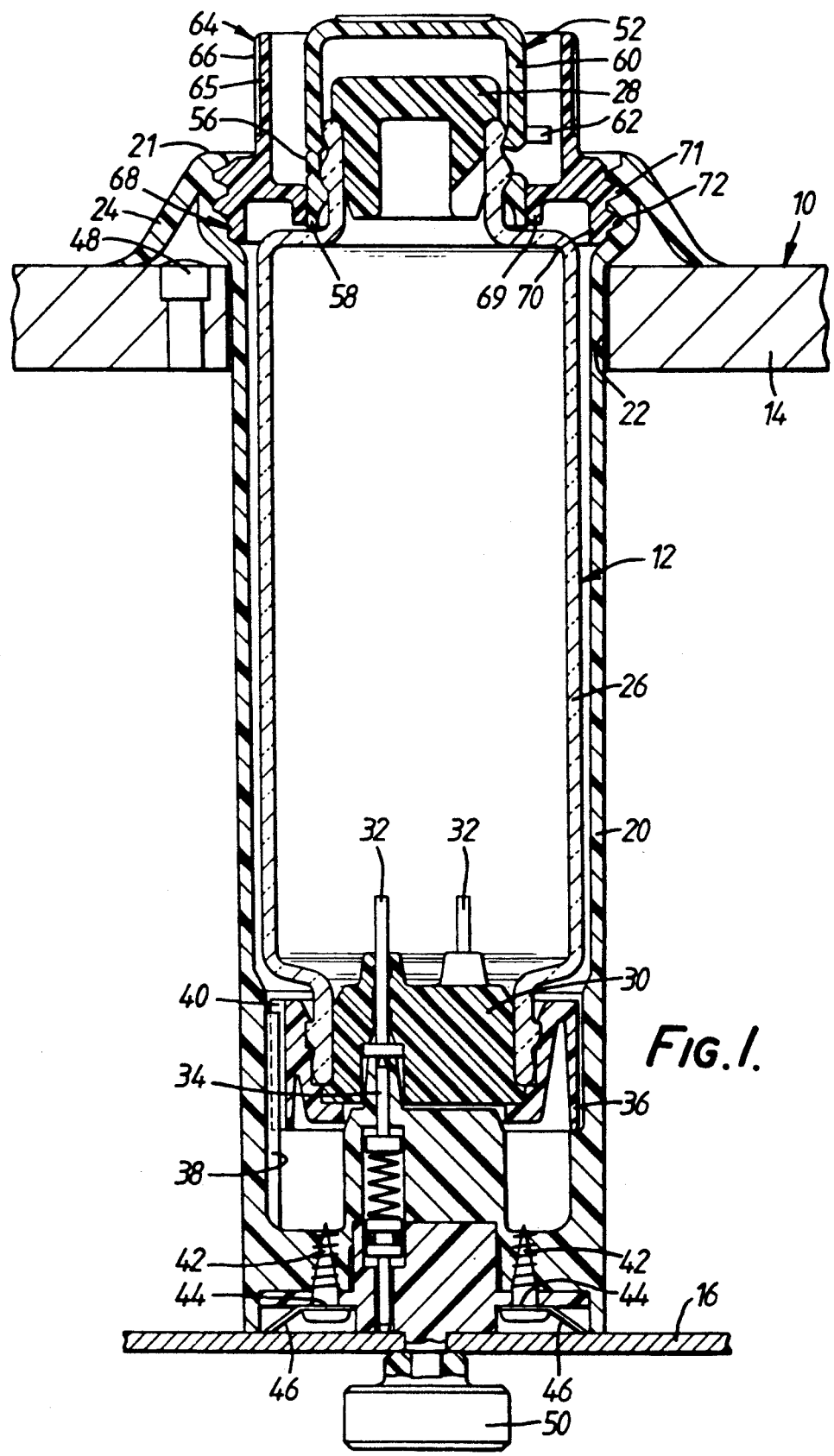
FIG. 1 illustrates a longitudinal cross-section through apparatus in accordance with the invention.

Referring to FIG. 1 of the drawings, there is shown one station of a container-mounting member 10 and a container 12 received by that station. The container-mounting member 10 comprises an array of, say, ninety-six such stations each intended to receive a single sample container 12.

The container-mounting member 10 generally comprises an upper support plate 14 and substantially parallel thereto and spaced therefrom is a base 16, comprising a printed circuit board. At each station of the container-mounting member where a sample container is to be received, there is a generally cylindrical vessel 20 extending between the base 16 upwardly through an aperture 22 in the upper support plate 14.

This vessel 20 is adapted to receive and locate a sample container 12 and is closed at its base for containment of spillage of sample material which may inadvertently occur. The upper rim 21 of vessel 20, which projects above the plate 14, turns back on itself and flares outwardly into a translucent skirt portion 24 which is in close sealing contact with the upper surface of the upper support plate 14. In this way leakage of any sample material which may have been spilt on the upper surface of the support plate 14 down into the container-mounting member via the aperture 22 in the support plate 14 is prevented.

The sample container 12 comprises a substantially cylindrical glass body 26 sealed at both ends by elastomeric bungs 28 and 30. The lower bung 30 houses a pair of electrodes 32 which make electrical connection with a respective pair of electrical contacts 34 provided on the container-mounting member.

A substantially cylindrical socket member 36 retains the lower bung 30 captive in the neck of the glass body 26 of the container 12, the socket member 36 being permanently retained on the glass body 26 by means of a crown-fitting. The outer cylindrical surface of the socket member 36 is of complementary cross-section and adapted to nest with the inner surface of the vessel 20, thereby providing a positive location means for the container at that particular station in the container-mounting member.

To ensure correct orientation of the electrodes 32 with their respective electrical contacts 34, there is provided orientation means between the socket member 36 and the vessel 20 in the form of an axially extending rib 38 on the inner surface of the vessel 20 adapted to key with a keyway in the form of a slot provided axially in the socket member 36.

The spillage containment vessel 20 houses, in its base, a pair of electrical probes 42 each in the form of a screw carrying, adjacent its head, a spring washer 44 having an integral tag 46 in contact with the printed circuit board 16. Applied across the two probes 42 is an electrical potential and any change in resistance will indicate the presence of sample material trapped in the base of the vessel 20. Spillage of even as little as 2 ml will be detected by the probes 42. An indicator light 48 is housed in the upper support plate 14 under the translucent skirt portion 24 of the spillage-containment vessel for protection against contamination ingress. The indicator light 48 is actuated by a change in resistance across the probes 42, thus showing that spillage has occurred in that particular containment vessel 20. The vessel 20 can then be removed from the container-mounting member 10 for cleaning or replacement. Each vessel 20 is releasably secured in the container-mounting member 10 by means of a nut and bolt 50 accessible from below the base 16.

The upper bung 28 of the sample container 12 is protected until the container is required for use by means of a tamper-proof cap 52. The cap 52 comprises a tear away ring 54 (see FIG. 2) most of which is removed in use leaving only a small portion 56 to act as a hinge between a neck portion 58, captive on the neck of the glass body 26 of the container 12 and a flip top portion 60 having a lug 62, which aids opening of the flip top 60.

Figure 3:
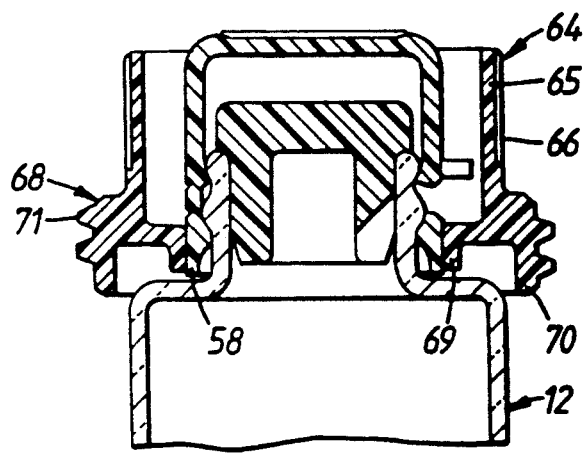
FIG. 3 is a partial longitudinal cross-section through a sample container into which sample material has been introduced, the container being ready for loading into the container mounting member.

In FIGS. 1 and 3 there is shown a collar 64 which co-operates with the upper rim 21 of the containment vessel 20 to form releasable retention means for retaining the sample container 12 in the container-mounting member. These releasable retention means are described in greater detail in our co-pending U.K. Patent Application No. 8602980. The collar 64 comprises a smaller diameter portion 65 having a knurled outer surface 66, and an enlarged diameter portion 68 having double walls 69,70. The outer wall carries a multi-start screw thread 71 for co-operation with a threadway 72 on the inner surface of the upper rim portion 21 of the vessel 20 (see FIG. 1). The inner wall 69 of the collar co-operates, with sliding friction, with the neck portion 58 of the tamper-proof cap 52.

Figure 4:
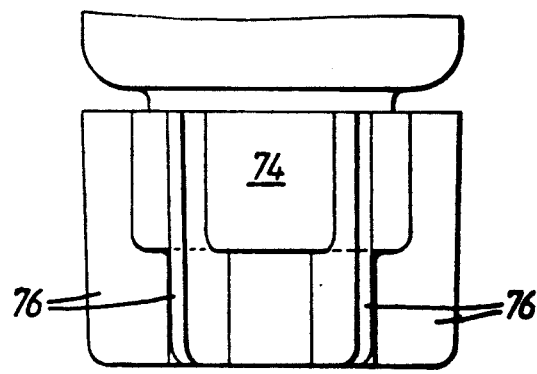
FIG. 4 illustrates, in partial perspective view, the lower portion of an alternative embodiment of sample container.

FIG. 4 illustrates an alternative embodiment of socket member 74 which is still of generally cylindrical configuration, but is provided with six fins 76 which extend laterally to co-operate with the inner surface of the containment vessel 20 when the container is received in the container-mounting member.

Figure 2:
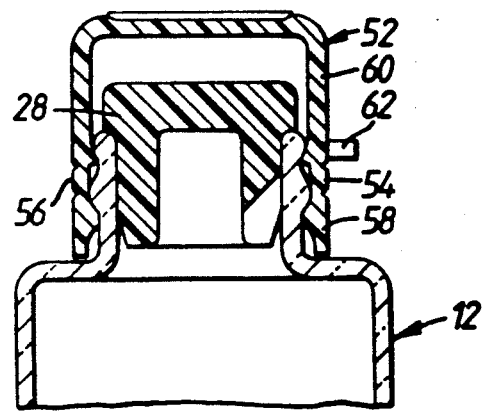
FIG. 2 is a partial longitudinal cross-section through a sample container before a sample has been introduced into the container.

In use of the apparatus, a container 12 in the form shown in FIG. 2 is taken and the tamper-proof cap 52 released by removal of the ring 54, the flip top 60 being hinged back by pushing upwardly on the tab 62. A sample, of blood for instance, can then be injected through the upper elastomeric bung 28 using a hypodermic needle. The flip top 60 is then returned to the position shown in FIGS. 1 and 3 and a collar 64 slipped over the tamper-proof cap 52 where it engages the neck portion 58 of the tamper-proof cap 52 with slipping friction. Until inserted in the container mounting member 10, the container 12 can be stood upright and is relatively stable in that position because of the shape of the socket member 36, which is substantially as wide as the glass body 26 which it supports.

The container 12 is then inserted into the container-mounting member 10 and is releasably retained therein by means of engagement between the collar 64 in screw-threaded engagement with the upper rim 21 of the container vessel 20. The socket member 36 ensures, by means of its nesting relation with the spillage containment vessel 20, a good positive location of the container 12 within the container-mounting member 10.

Any inadvertent spillage of sample material into the containment vessel is detected by means of probes 42 and indicated by indicator light 48.

We claim:

1. Apparatus for detecting micro-organisms in a sample, comprising;
    container means for holding a sample and having first and second electrodes contactable with a sample for the detection of micro-organisms therein;
    an outer vessel within which the container means is received and supported and within which spillage of sample material from the container means is contained; and detection probe means located in the outer vessel for the detection of any such spillage.

2. Apparatus as claimed in claim 1, wherein the detection probe means comprises electrical probes located in the base of the vessel, and the apparatus further comprising means for applying an electrical potential across said electrical probes whereby a change of resistance between the probes indicates presence of spillage in the vessel.

3. Apparatus as claimed in claim 1, wherein the container further comprises an elastomeric bung through which sample material may be injected into the container and tamper-proof cap means protecting the bung until the container is required for use.

4. Apparatus as claimed in claim 3, further comprising a removable collar, co-operable with said tamper-proof cap means by slipping friction, and provided with interengagement means co-operable with the outer vessel for releasable retention of the container by the outer vessel.

5. Apparatus for detecting micro-organisms in a sample, comprising:
container means for holding a sample and having first and second electrodes contactable with a sample for the detection of micro-organisms therein;
an outer vessel within which the container means is received and supported and within which spillage of sample material form the container means is contained;
detection probe means located in the outer vessel for the detection of any such spillage; and
a socket member of complementary cross-section with the outer vessel and adapted to embrace the outer vessel in nesting relation to said outer vessel.

6. Apparatus for detecting micro-organisms in a sample, comprising:
container means for holding a sample and having first and second electrodes contactable with a sample for the detection of micro-organisms therein;
an outer vessel within which the container means is received and supported and within which spillage of sample material form the container means is contained;
detection probe means located in the outer vessel for the detection of any such spillage;
a socket member of complementary cross-section with the outer vessel and adapted to embrace the outer vessel in nesting relation to said outer vessel;
an outer surface of the socket member nests with an inner surface of the outer vessel; and
said socket member outer surface being substantially right cylindrical and having an axial extent less than its diameter.

7. Apparatus for detecting micro-organisms in a sample, comprising:
container means for holding a sample and having first and second electrodes contactable with a sample for the detection of micro-organisms therein;
an outer vessel within which the container means is received and supported and within which spillage of sample material from the container means is contained;
detection probe means located in the outer vessel for the detection of any such spillage;
a socket member of complementary cross-section with the outer vessel and adapted to embrace the outer vessel in nesting relation to said outer vessel;
said outer vessel comprising electrical contact means for electrical connection with at least said first electrode of the container means; and
orientation means between the socket member and the outer vessel, whereby when the container means is received by the outer vessel, the firs electrode is at a predetermined orientation to the outer vessel and, hence, to the or each respective electrical contact means.

8. Apparatus for detecting micro-organisms in a sample, comprising;
container means for holding a sample and having first and second electrodes contactable with a sample for the detection of micro-organisms therein;
an outer vessel within which the container means is received and supported and within which spillage of sample material from the container means is contained;
detection probe means located in the outer vessel for the detection of any such spillage;
a socket member of complementary cross-section with the outer vessel and adapted to embrace the outer vessel in nesting relation to said outer vessel;
said outer vessel comprising electrical contact means for electrical connection with at least said first electrode of the container means;
orientation means between the socket member and the outer vessel, whereby when the container means is received by the outer vessel, the first electrode is at a predetermined orientation to the outer vessel and, hence, to the or each respective electrical contact means; and
said orientation means comprises a key and keyway, one of which is provided on the socket member and the other on the outer vessel.

9. Apparatus for detecting micro-organisms in a sample, comprising:
container means for holding a sample and having first and second electrodes contactable with a sample for the detection of micro-organisms therein;
an outer vessel within which the container means is received and supported and within which spillage of sample material form the container means is contained;
detection probe means located in the outer vessel for the detection of any such spillage;
said detection probe means comprises electrical probes located in the base of said outer vessel; and
means for applying an electrical potential across said electrical probes whereby a change of resistance between the probes indicates presence of spillage in the outer vessel.

10. Apparatus for detecting micro-organisms in a sample, comprising;
container means for holding a sample and having first and second electrodes contactable with a sample for the detection of micro-organisms therein;
an outer vessel within which the container means is received and supported and within which spillage of sample material from the container means is contained;
detection probe means located in the outer vessel for the detection of any such spillage;
· an elastomeric bung through which sample material may be injected into the container means;
tamper-proof cap means protecting the bung until the container mans is required for use;
a removable collar co-operable with said tamper-proof cap means by slipping friction; and
provided with interengagement means co-operable with the outer vessel for releasable retention of the container means by the outer vessel.

* * * * *